(12) United States Patent
Maubois et al.

(10) Patent No.: US 8,937,043 B2
(45) Date of Patent: Jan. 20, 2015

(54) METHOD FOR OBTAINING A TGF-BETA ENRICHED PROTEIN FRACTION IN ACTIVATED FORM, PROTEIN FRACTION AND THERAPEUTIC APPLICATIONS

(75) Inventors: Jean-Louis Maubois, Pace (FR); Jacques Fauquant, Pleumeleuc (FR); Pierre Jouan, Cesson Sevigne (FR); Michel Bourtourault, Noyal Châtillion sur Seiche (FR)

(73) Assignee: Piere Jouan Biotechnologies S.A., Rennes (FR)

( * ) Notice: Subject to any disclaimer, the term of this patent is extended or adjusted under 35 U.S.C. 154(b) by 1053 days.

(21) Appl. No.: 11/181,139

(22) Filed: Jul. 13, 2005

(65) Prior Publication Data
US 2005/0250697 A1     Nov. 10, 2005

Related U.S. Application Data

(62) Division of application No. 10/469,530, filed as application No. PCT/FR02/02489 on Jul. 12, 2002, now Pat. No. 7,141,262.

(30) Foreign Application Priority Data

Jul. 13, 2001 (FR) ..................................... 01 09390

(51) Int. Cl.
    *A61K 38/18*          (2006.01)
    *A61K 38/24*          (2006.01)
    (Continued)

(52) U.S. Cl.
    CPC ................. *A61K 35/20* (2013.01); *A23J 1/205* (2013.01); *A61K 38/1841* (2013.01); *C07K 14/495* (2013.01); *A23V 2002/00* (2013.01); *Y10S 930/12* (2013.01)
    USPC .............................. 514/8.9; 530/399; 930/120

(58) Field of Classification Search
    USPC .......................................... 514/8.9; 530/399
    See application file for complete search history.

(56) References Cited

U.S. PATENT DOCUMENTS

| 3,721,570 A | 3/1973 | Linteris |
| 3,791,283 A | 2/1974 | Moreno et al. |

(Continued)

FOREIGN PATENT DOCUMENTS

| AU | WO 96/34614 | * 11/1996 | ............. A61K 35/20 |
| CH | WO 97/34929 | * 9/1997 | ........... C07K 14/475 |

(Continued)

OTHER PUBLICATIONS

Jin et al. "Separation, Purification, and Sequence Identification of TGF-B1 and TGF-B2 from Bovine Milk" Journal of Prorein Chemistry, vol. 10, No. 5, 1991.*

(Continued)

*Primary Examiner* — Patricia A Leith
*Assistant Examiner* — Erin M Bowers
(74) *Attorney, Agent, or Firm* — Sutherland Asbill & Brennan LLP

(57) ABSTRACT

The invention concerns a method for obtaining a highly enriched TGF-beta protein fraction in activated form, from a liquid solution rich in proteins said to be soluble in the aqueous phase of milk and/or of whey, said method comprising the following steps; a) adjusting soluble proteins purified at a concentration between 5 and 30 g/liter of solution; b) precipitating part of the whey proteins by acidic treatment of the solution thus obtained to a pH ranging between 4 and 5.5 and at a temperature ranging between 55° C. and 68° C.; c) carrying out a microfiltration of the treated solution by diafiltration, so as to obtain respectively a microfiltration retentate and a microfiltrate; d) recuperating the microfiltration retentate containing the protein fraction highly enriched in TGF-beta; e) drying the microfiltration retentate which has been subjected to diafiltration to obtain a powder highly enriched in TGF-beta.

7 Claims, 1 Drawing Sheet

(51) Int. Cl.
*A61K 35/20* (2006.01)
*A23J 1/20* (2006.01)
*C07K 14/495* (2006.01)

(56) References Cited

U.S. PATENT DOCUMENTS

| | | | |
|---|---|---|---|
| 3,883,448 A | 5/1975 | Sternberg | |
| 3,922,375 A | 11/1975 | Dalan et al. | |
| 3,997,447 A | 12/1976 | Breton et al. | |
| 4,029,825 A | 6/1977 | Chang | |
| 4,105,547 A | 8/1978 | Sandblom | |
| 4,140,810 A | 2/1979 | van Dam et al. | |
| 4,352,828 A | 10/1982 | Rialland et al. | |
| 4,462,989 A * | 7/1984 | Cerami | 424/431 |
| 4,847,096 A | 7/1989 | Mellqvist et al. | |
| 4,956,102 A | 9/1990 | Allsing | |
| 5,017,372 A | 5/1991 | Hastings | |
| 5,037,532 A | 8/1991 | Winter et al. | |
| 5,047,249 A * | 9/1991 | Rothman et al. | 424/543 |
| 5,122,536 A * | 6/1992 | Perricone | 514/474 |
| 5,221,734 A * | 6/1993 | Burk et al. | 530/399 |
| 5,256,437 A | 10/1993 | Degen et al. | |
| 5,401,523 A | 3/1995 | Degen et al. | |
| 5,527,350 A * | 6/1996 | Grove et al. | 607/89 |
| 5,981,606 A * | 11/1999 | Martin | 514/724 |
| 6,036,979 A | 3/2000 | Hormann et al. | |
| 6,139,901 A | 10/2000 | Blazey et al. | |
| 6,177,550 B1 * | 1/2001 | Meyer et al. | 530/412 |
| 6,312,755 B1 | 11/2001 | Wu | |
| 6,375,014 B1 | 4/2002 | Garcera et al. | |
| 7,141,262 B2 | 11/2006 | Maubois et al. | |
| 2004/0219225 A1 | 11/2004 | Kivits et al. | |
| 2008/0031969 A1 | 2/2008 | Juneau et al. | |

FOREIGN PATENT DOCUMENTS

| | | |
|---|---|---|
| EP | 0 313 515 B1 | 4/1989 |
| EP | 0 527 283 B1 | 2/1993 |
| EP | 1 052 013 A1 | 11/2000 |
| FR | 2 692 441 | 12/1993 |
| SE | 7416257-9 | 9/1977 |
| WO | 01/25276 | 4/2001 |
| WO | PCT/NL00/00719 | 4/2001 |
| WO | WO 01/25276 A1 | 4/2001 |
| WO | 03/008447 | 1/2003 |
| WO | 2007/012748 | 2/2007 |
| WO | 2007/038870 | 4/2007 |

OTHER PUBLICATIONS

Wright et al. "Scarring alopecia in psoriasis" Acta Derm Venereol. 1990; 70(2) 156-9.*

Rogers et al., J. Endocrinol. 151: 77-86 (1996).*

Aattouri N. et al., 2004, "Immunosuppressive Effect of a Milk-derived Extract.", 12th International Congress of Immunology and 4th Annual Conference of FOCIS, Reprinted from: Immunology 2004, Medimond, International Proceedings, pp. 1-4.

Drouin R. et al., 2007, "XP-828L (Dermylex), a new whey protein extract with potential benefit for mild to moderate psoriasis.", Can. J. Physiol. Pharmacol., 85: 943-951.

Poulin Y. et al., 2005, "Safety and Efficacy of a Mild-derived Extract in the Treatment of Plaque Psoriasis: An Open-label Study.", Journal of Cutaneous Medecine and Surgery, pp. 271-275.

Poulin Y. et al., 2006, "XP-828L in the treatment of Mild to Moderate Psoriasis: Randomized, Double-Blind, Placebo-Controlled Study.", Journal of Cutaneous Medecine and Surgery, vol. 10, No. 5.

M.I. Rogers, et al: "Transforming growth factor beta in bovine milk: concentration, stability and molecular mass forms," Journal of Endocrinology, 1996, pp. 77-86, vol. 151, Journal of Endocrinology Ltd., XP000644717 Bristol, GB.

Ruo-Jun Xu, et al: "Detection and Characterisation of Transforming Growth Factor-Beta in Porcine Colostrum," Biology of the Neonate, Jan. 1999, pp. 59-64, vol. 75, Dep. Zool., Univ. Hong Kong, Hong Kong.

Y. Jin, et al: "Separation Purification and Secquence Identification of TGF-Beta-1 and TGF-Beta-2 from Bovine Milk," Journal of Protein Chemistry, 1991, pp. 565-575, vol. 10, Dep. Biotechnology, Pharmaceutical Res. Div. Ciba-Geigy Ltd., Basel, Switzerland.

Chiba, Hideo, et al: "Biologically Functional Peptides from Food Proteins: New Opioid Peptides from Milk Proteins," pp. 123-153, Kyoto Univ, Dept. of Food Science and Techn., Kyoto, Japan, 1986.

Pellegrini, Antonio, et al: "Isolation and Identification of Three Bactericidal Domains in the Bovine a-Lactalbumin Molecule," Biochimica et Biophysica Acta 1426, 1999, pp. 439-448.

* cited by examiner

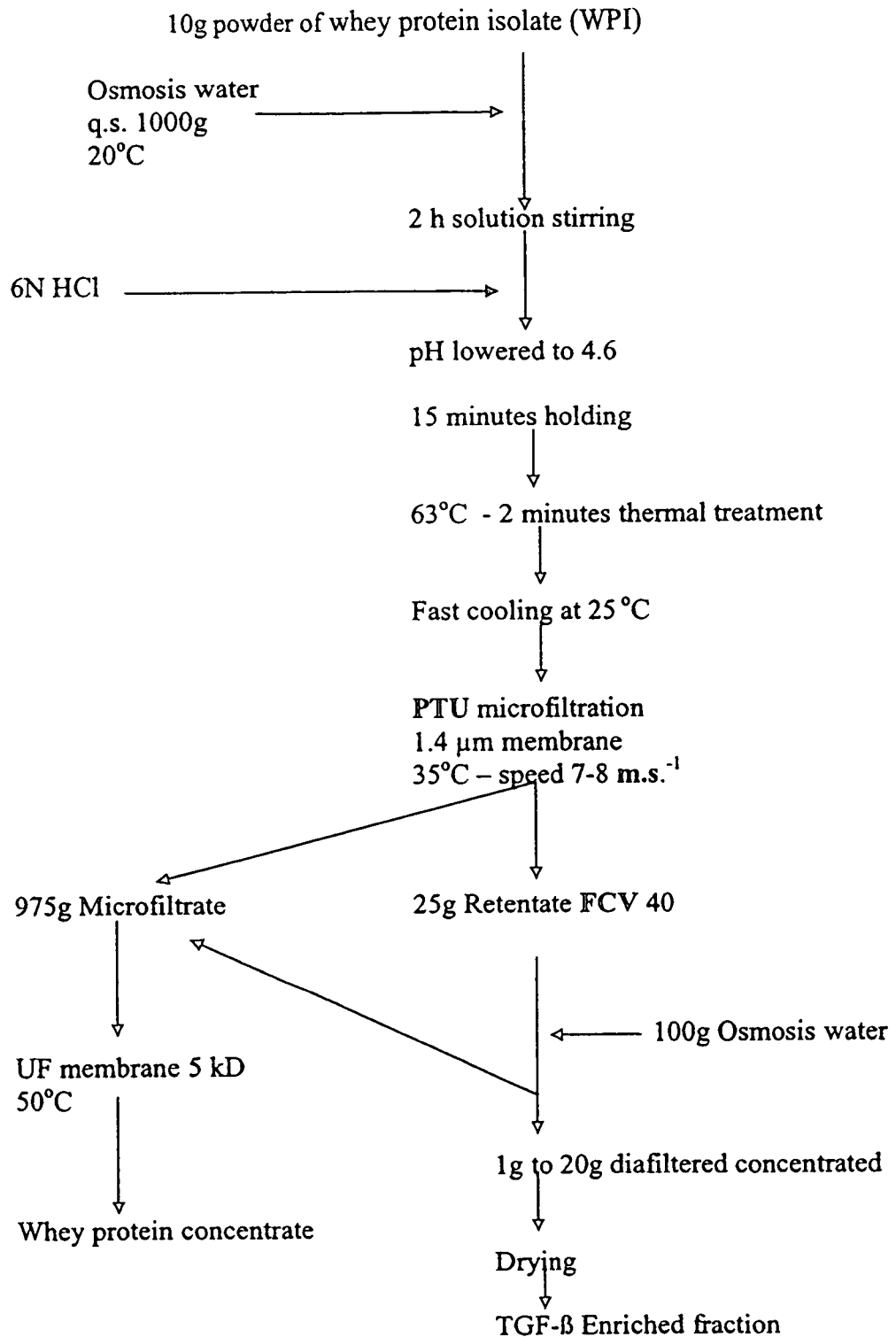

METHOD FOR OBTAINING A TGF-BETA ENRICHED PROTEIN FRACTION IN ACTIVATED FORM, PROTEIN FRACTION AND THERAPEUTIC APPLICATIONS

RELATIONSHIP TO PRIOR APPLICATION

This application is a divisional of U.S. patent application Ser. No. 10/469,530, having a 371 (c) date of Dec. 22, 2003, which is the National Stage of PCT/FR02/02489 filed Jul. 12, 2002.

BACKGROUND OF THE INVENTION

1. Technical Field

This invention relates to the field of TGF-beta factor purification from a dairy source.

2. Description of Prior Art

Milk, in particular human and mammal milk, contains several bioactive polypeptides, especially numerous growth factors. One of these growth factors contained in milk is TGF-beta (Transforming Growth Factor beta).

The term TGF-beta designates a family of different growth factors. TGF-beta 1 and TGF-beta 2 are two homologous forms of TGF-beta. They are homodimeric constituents made up of two similar polypeptide chains each containing 112 amino-acids, linked by a disulfide bridge. Their molecular mass is 25,000 Daltons. TGF-beta 1 and TGF-beta 2 have 72% of structural homology and they present similar biological properties. Bovine and Human TGF-beta 2 are identical in respect of their amino-acid sequence.

TGF-beta can be obtained by genetic recombination in purified form. But preparations containing TGF-beta recombinants are susceptible to contain some bacterial proteins, of which some are allergenic. In addition, by definition, purified preparations of TGF-beta recombinants do not contain associated milk proteins which can complete or increase the TGF-beta biological effect.

Cow's milk contains both TGF-beta 1 or TGF-beta 2. TGF-beta 2 is the main component and represents 90% in weight of TGF-beta found in milk, while TGF-beta 1, on the other hand, represents 10% in weight of the total TGF-beta content in milk.

In milk, more than 90% of the TGF-beta 2 is in latent form, i.e. in a non-biologically active form.

Various scientific studies have shown that TGF-beta content in milk is from 12 to 150 µg/l in colostrum, from 3.7 to 3.8 µg/l in crude and pasteurized milk, 4.3 µg/l in skimmed milk, and 3.7 µg/l in whey.

Biological activities of TGF-beta are numerous, which give to this polypeptide a great therapeutical interest for prevention or treatment of a large variety of diseases or pathologies.

TGF-beta is biologically active on the extra-cellular matrix. It stimulates the synthesis of matrix proteins and increases the synthesis of collagen and fibronectin in fibroblasts. It also has an inhibitory effect on the synthesis of proteolytic enzymes such as collagenase and metalloproteases. TGF-beta increases the secretion of protease inhibitors such as the plasminogen activator inhibitor or metalloprotease inhibitors.

TGF-beta has also a biologic activity on the skeleton. In particular, TGF-beta is in high concentration in bones. It has an activity on cartilage formation, stimulates the resorption of osteoclasts, and the activation of osteoblasts. It acts as a natural inhibitor of the resorption of bones and provides bone formation stimulation.

TGF-beta is also active towards lymphocytes. By way of illustration, it inhibits T-lymphocytes proliferation and contributes to the activity of so-called "Natural Killers" cells.

TGF-beta is also a powerful anti-inflammatory agent. It decreases pro-inflammatory cytokines production. It has immunosuppresive properties and inhibits the proliferation of activated T-lymphocytes.

In addition, TGF-beta has antiproliferative effects. It is a strong inhibitor of epithelial cells. TGF-beta has a strong anti-mitogenic activity towards mesenchym cells, embryonic fibroblasts, endothelial cells, and T and B lymphocytes. It also has a strong inhibitory effect on the growth of hepatocytes, and could possibly have an important role in maintaining the quiescent state of thereof. TGF-beta also acts as a negative regulation factor of the mammary epithelium.

TGF-beta also has anticancer effects. During carcinogenesis, cancer cells can loose their ability to respond to TGF-beta. Nevertheless, some epithelial cell tumors, like breast cancer cells, are sensitive to anti-proliferative effects of TGF-beta. Such is the case for breast cancer cells.

TGF-beta also acts on proliferation and differentiation of leukemia cells. It inhibits the proliferation of promyelocyte cells. It could have a synergistic effect with retinoic acid and vitamin D3.

European patent application No. EP 0 527.283 in the name of Société des Produits NESTLE S.A. describes a process for preparing a milk-derived product containing TGF-beta. During this process, the crude milk is skimmed by centrifugation, desalted on a PD-10 (Pharmacia) chromatographic column, and then sterilized by filtration on a "Millipore" membrane with a 0.2 µm pore diameter. The skimmed milk is sterilized, adjusted at pH 4.0 with 1N HCl, and then centrifuged at 40,000 g during 60 minutes to separate precipitated casein from whey. The separated whey is neutralized by 1N sodium hydroxide and dialyzed. However, this process, which is able to eliminate casein from the initial skimmed milk, is not a process to purify TGF-beta. In fact, the final product contains all the whey proteins from the initial milk, where the TGF-beta is, but without significant enrichment of this specific protein.

In the state of the art, many processes of obtaining protein fractions enriched in TGF-beta from milk have been described.

European patent application EP 0 313.515 in the name of CIBA GEIGY describes a process for purification of a growth factor contained in milk, with successive chromatographic steps, especially cation exchange resins, hydrophobic interaction chromatography (RP-HPLC) or size exclusion chromatography supports.

The PCT application No. WO 01 25.276 in the name of CAMPINA MELKUNIE B.V. describes a process for extracting TGF-beta and similar to insulin growth factors (IGF-1) from a dairy product. This process comprises the following steps:

a) recovering a base fraction of the dairy product by cation exchange chromatography;

b) passing the fraction obtained in step a) on a hydroxyapatite column; and c) elution of the hydroxyapatite column with suitable eluents selected so as to obtain for example a TGF-beta fraction substantially free of IGF-1.

All the processes described above have technical disadvantages. As a matter of fact, TGF-beta purification processes involving successive chromatographic steps are long and tedious. The important number of chromatographic steps necessary for achieving a desired degree of purity considerably decreases the final yield because of the progressive TGF-beta degradation while purification is carrying out, and the unavoidable loss of biologically active TGF-beta at each of the chromatography steps. In addition to the use of different saline and highly polluting regeneration solutions that must thereafter be eliminated, these processes present a high risk of bacterial contamination of the final product.

There is therefore a need in the state of the art for improved processes allowing the purification of TGF-beta from a dairy product, without the disadvantages mentioned above of the processes currently available in the art.

SUMMARY OF THE INVENTION

An object of the invention is a method for obtaining a protein fraction highly enriched in TGF-beta in activated form from a liquid solution rich in proteins so-called soluble of the aqueous phase of milk and/or whey, said method comprising the following steps:
  a) adjusting purified soluble proteins at a concentration between 5 and 30 g/liter of solution;
  b) precipitating part of the whey proteins by acid treatment of the solution thus obtained to a pH ranging between 4 and 5.5 and at a temperature ranging between 55° C. and 68° C.;
  c) carrying out a microfiltration of the treated solution with diafiltration, so as to obtain respectively a microfiltration retentate and a microfiltrate;
  d) recovering the microfiltration retentate containing the protein fraction highly enriched in TGF-beta; and
  e) drying the microfiltration retentate which has been subjected to diafiltration to obtain a powder highly enriched in TGF-beta.

Preferentially, the adjusting step a) is performed by diluting a solution containing the soluble milk proteins, like a whey protein isolate; also designated as "WPI".

Preferentially, the precipitating step b) is carried out at a temperature ranging between 60° C. and 68° C. and, more preferentially, of about 63° C.

Advantageously, the length of the precipitation step b) is ranging between 30 seconds and 10 minutes, preferentially between 30 seconds and 5 minutes, and is more preferentially, of about 2 minutes.

In a preferred embodiment, the microfiltration of step c) is carried out with a microfiltration membrane with an average pore size comprised between 0.8 and 1.6 µm and having a narrow pore size distribution.

Another object of the present invention is to provide a protein fraction highly enriched in TGF-beta, susceptible to be obtained by the process above.

It also relates to a pharmaceutical composition comprising a protein fraction such as defined above, added if necessary with one or more physiologically compatible excipients.

The present invention also concerns the use of a protein fraction such as defined above for a drug preparation for prevention or treatment of various pathologies for which TGF-beta is an interesting therapeutical compound.

BRIEF DESCRIPTION OF THE DRAWING

FIG. 1 illustrates a scheme of the method according to the invention for obtaining a protein fraction enriched in TGF-beta.

DESCRIPTION OF PREFERRED EMBODIMENT

The applicant developed a simple and rapid method for obtaining a protein fraction highly enriched in TGF-beta from a liquid solution rich in whey proteins.

The term TGF-beta means an association or a mixture of TGF-beta comprising at least 90% in weight of TGF-beta 2 and at most 10% in weight TGF-beta 1.

In particular, the method according to the invention comprises a small number of short length steps, making it possible to avoid a significant loss of biological activity related to a protein degradation in the course of time during the purification process.

Moreover, the process according to the invention does not comprise any chromatographic step which would necessitate successive adsorption of the interesting proteins on several substrates, then their desorption from the substrates by elution, which compulsorily involves a significant loss of TGF-beta and thus harmful consequences on the process final yield.

The present invention concerns a method for obtaining a protein fraction enriched in TGF-beta from a liquid solution rich in proteins, said method comprising the steps of
  a) adjusting purified whey proteins at a concentration between 5 and 30 g/liter of solution;
  b) precipitating part of the whey proteins by acid treatment of the liquid solution at a pH ranging between 4 and 5.5 and at a temperature ranging between 55° C. and 68° C.;
  c) carrying out a microfiltration of the treated solution with diafiltration, so as to obtain respectively a microfiltration retentate and a microfiltrate;
  d) recovering the microfiltration retentate containing the protein fraction highly enriched in TGF-beta; and
  e) drying the microfiltration retentate diafiltrated to obtain a powder highly enriched in TGF-beta.

The starting solution rich in whey proteins can be of different types. Preferentially, it is a whey protein isolate (WPI), which can be prepared by all methods known to one skilled in the art.

The solution rich in whey proteins has, preferentially, the following composition:
  Total nitrogeneous matter: 10 g/Kg.
  Dry extract: 10.4 g/Kg.
Thus 96% of proteins are in the dry extract.
Step a) of the Method Step a) of the method consists preferentially of a dilution step of the proteins with osmosis water to obtain a concentration of 5 to 30 g of proteins per kilograms of solution.
Step b) of the Process Step b) consists of a fractioned precipitation step of the whey proteins in operating conditions allowing a selective precipitation of the protein fraction containing the almost totality of the TGF-beta which was initially contained in the liquid rich in whey proteins, e.g. a WPI.

The goal was reached by the applicant by combining some pH and temperature parameters.

It was found, according to the invention, that applying only one of these parameters, either the pH or the temperature, does not allow to reach the desired degree of protein precipitation.

When step b) is carried out at a temperature below 55° C., the precipitation of the protein fraction rich in TGF-beta is not obtained. Also, when the temperature of the treatment was above 68° C., and for increasing temperatures, the co-precipitation, with TGF-beta, of an increasing fraction of whey proteins is observed. Thus, for a temperature of above 70° C., the quasi totality of the whey proteins initially contained in the initial solution is precipitated and the selective enrichment in TGF-beta is not anymore obtained.

By way of illustration, at pH of 4.6, precipitation results observed for increasing temperatures are shown in Table 1 below.

Table 1 below summarizes the evolution of the TGF-beta and whey protein precipitation at pH of 4.6 as a function of the thermal treatment intensity (length of the treatment: 2 minutes).

TABLE 1

| Temperature (° C.) | % of initial TGF-beta[a] | % of other proteins precipitated[b] |
|---|---|---|
| 25° C. | 40% | 10% |
| 50° C. | 43% | 12% |
| 60° C. | 67% | 15% |
| 63° C. | 84% | 16% |
| 65° C. | 94% | 30% |
| 70° C. | 100% | 50% |

[a]Pourcentage of TGF-beta initially contained in the liquid solution rich in whey proteins (WPI) which is found in the precipitated protein fraction.
[b]Pourcentage of total proteins initially contained in the liquid solution rich in whey proteins (WPI) which is found in the precipitated protein fraction precipitated.

The results of Table 1 show that at pH of 4.6 and at a temperature of 50° C., only 43% of the TGF-beta initially contained in the solution rich in whey proteins is precipitated. At a temperature of 70° C., 100% of the initial TGF-beta is precipitated, but the precipitation is poorly selective since 50% of the total proteins initially contained in the initial solution of whey proteins co-precipitate with TGF-beta, which does not allow to reach the desired enrichment degree in TGF-beta.

Preferentially, step b) of the method according to the invention is carried out at a pH comprised between 4 and 5.5 and in a more advantageous manner at a pH between 4 and 5. In the most preferred embodiment, step b) of the method is carried out at a pH comprised between 4.3 and 4.9, yet better between 4.4 and 4.8, preferentially between 4.5 and 4.7. The optimal processing pH is about 4.6.

Preferentially, the pH is adjusted with a concentrated acid to maximally reduce the dilution phenomena following the addition of further volume of solution. Preferentially, a concentrated HCl solution is used and in the most preferred manner a 6N HCl solution is used particularly since its handling is easier and less dangerous than for other concentrated acids.

The processing temperature in step b) is advantageously comprised between 55° C. and 68° C., preferentially between 61° C. and 65° C., in a preferred manner between 62° C. and 64° C. and in the most preferred embodiment about 63° C.

Without wishing to be bound by any particular theory, the applicant believes that TGF-beta, which is mainly found in its latent form in the starting solution of whey proteins, is converted in its activated form (biologically active) during step b) of the method.

The combination of temperature and pH parameters above allows to perform the precipitation step for a short period of time, thus avoiding the TGF-beta degradation. Thus, the duration of the precipitation step b) is comprised between 30 seconds and 10 minutes, preferentially between 30 seconds and 5 minutes, yet better between 1 minute and 3 minutes, and in the most preferred embodiment of about 2 minutes.

When step b) of the method is carried out during 15 minutes at pH of 7.0 at 80° C., a TGF-beta denaturation is observed, this denaturation being increasing with the precipitation step length above 15 minutes.

The thermal treatment can be of all kind. It is preferentially carried out with tubular or scraped surface heat exchangers known to one skilled in the art for thermal treatments of viscous solutions or suspensions like fresh cheeses.

In a specific embodiment of step b) of the process, the precipitated solution of TGF-beta is quickly cooled down.

The applicant observed that a quick cooling after precipitation has a positive impact on the texture of the precipitate obtained and supports consequently the processing of the subsequent method steps, particularly the microfiltration step, since the precipitate should not be too fine in order to avoid filling in the membrane.

Preferentially, the cooling is carried out in a tubular or plate heat exchanger, with water at room temperature, preferentially between 20° C. and 30° C., advantageously about 25° C.

The length of the cooling step is preferentially comprised between 1 and 20 minutes, and in the most preferred manner between 2 and 10 minutes.

The final product of step b) is thus a liquid containing a suspension of precipitated proteins including TGF-beta in a solution of non-precipitated whey proteins.

Step c) of the Process

The protein suspension containing TGF-β in a solution of non-precipitated whey proteins obtained in step b) is microfiltered with diafiltration.

The precipitate is submitted to a microfiltration step with diafiltration in order to remove most of the remaining whey soluble proteins while concentrating the protein fraction of interest containing mainly TGF-β.

In order to avoid significative losses of TGF-β while removing most of the non-desired soluble whey proteins, the microfiltration step is carried out using a membrane having a narrow gaussian pore size distribution.

Microfiltration is carried out preferably with a microfiltration membrane having an average pore size comprised between 0.8 and 1.6 μm and having a narrow gaussian pore size distribution.

In the most preferred manner, the microfiltration with diafiltration is performed in conditions such as the transmembrane pressure is kept uniform over the whole filtration membrane surface.

Co-current recirculation of the permeate represents a first embodiment of achieving the microfiltration step of the process according to the invention providing a transmembrane pressure substantially uniform over the whole filtration membrane surface.

Thus, the co-current recirculation of the permeate at the outer surface of the filtration membrane support allows the generation of a pressure drop (difference between inlet and outlet pressures of fluids circulating on each side of the filtration membrane) identical in each filter compartment and identical in each point of the filtration membrane over the whole filtration surface. The technique of co-current recirculation of the permeate is for example described in the Swedish Patent no SW 74 16 257 (Sandblom).

When co-current recirculation of the permeate is applied and a uniform transmembrane pressure is desired, better results are obtained with mineral or ceramic membranes such as those made of alpha-alumina commercialized by Société des Céramiques Techniques (France), under the brand Membralox or by Société Orelis (France) under the brand KERASEP or yet membranes under the brand STERILOX.

In another aspect, the filtration membrane is placed on a macroporous support having a longitudinal permeability gradient. This support possesses a constitution such as it has a porosity gradient that decreases from one end of the filtration membrane to the other.

Due to this filter support, the hydraulic resistance decreases from one end of the filtration membrane to the other and it generates a uniform transmembrane pressure all along the membrane path.

Such filter type is advantageously made from ceramic such as the support filter described in French patent application no FR 97 04 359.

In another aspect, dynamic membrane filtration can also be achieved such as described in French patent FR 93 06 321 (publication 2 692 441), for example by using organic membranes.

Accordingly to such a mode of carrying out the method of the invention, the filtration membrane and its support are placed on a rotating axis, said device being completed with a rotating disk placed at a short distance from the microfiltration membrane.

The rotation of the disk placed at a short distance (about 4 mm) from the microfiltration membrane generates a shear stress of 50 to 100 times stronger than for classical cross-flow filtration, the shear stress acting in the three dimensions (radial, tangential, and axial). In such a device, the shear stress generation to the lining is decoupled from the transmembrane pressure. Such processes of dynamic membrane filtration are also described in U.S. Pat. Nos. 5,037,532, 3,997,447 and 4,956,102.

In a preferred embodiment, the microfiltration membrane possesses an average pore size comprised between 1 and 1.6 μm, and in the most preferred embodiment around 1.4 μm, such as the one commercialized by the company EXEKIA under the reference "STERILOX 1.4 μm classic" or under the reference "STERILOX 1.4 μm GP", which requires the processing, in the microfiltration equipment, of the co-current recirculation of the microfiltrate to obtain a uniform transmembrane pressure.

Preferably, the diafiltration is performed using osmosis water or demineralized water, sterilly filtered.

Preferably, the diafiltration is achieved by using between 1 and 6 dia-volumes, preferably about 4 diavolumes, in order to obtain a maximal elimination of soluble whey proteins other than TGF-β.

Preferentially, the microflitration with diafiltration is performed at a pH comprised between 4 and 5.5, preferably between 4.3 and 5, and in the most preferred manner at a pH of about 4.6 which allows to maintain the TGF-beta in the precipitated form.

The pH adjustment is achieved with a concentrated acid, preferably concentrated HCl, advantageously at 6N concentration.

The final products of the microfiltration step by diafiltration are respectively:
on one hand a retentate highly enriched in TGF-β, and
on the other hand, a microfiltrate containing soluble whey proteins.

For example, the microfiltrate contains 8.0 g/l of said soluble proteins for a dry matter content around 8.8 g/l. Those whey proteins that have not been precipitated can advantageously be further concentrated using any technique known to one skilled in the art, ultrafiltration over membranes, for example, and be used, once concentrated, for most WPI conventional applications.

Recovering of the Microfiltration Retentate

After the steps of microfiltration with diafiltration, the microfiltration retentate is recovered and constitutes the protein fraction highly enriched with TGF-beta.

Usually, this microfiltration retentate contains from 6.5 to 17 μg/l of TGF-beta per 1 g of total proteins.

Advantageously, the microfiltration retentate, after its recovery, is dried by any technique known to a man skilled in the art (lyophilisation, spray-drying . . . ) to obtain the protein fraction highly enriched in TGF-beta under a powder form.

The retentate powder contains approximately 15% of the initial whey proteins of the starting solution. The combination of all process steps according to the invention allows the elimination of 85% of the whey proteins initially contained in the initial solution. In this powder, the TGF-beta content is usually comprised between 6.5 and 17 μg/g of powder, which approximately corresponds to the recovery of 70% of the TGF-beta initially contained in the starting whey protein solution. The concentration in TGF-beta 2 comparatively to the powder weight corresponds to a concentration in TGF-beta 2 of 6 to 15 μg per gram of total proteins contained in the powder.

This protein fraction highly enriched in TGF-beta can be used as such and, if necessary, in association with one or many physiologically compatible excipients.

This protein fraction highly enriched in TGF-beta can also be subject to additional purification steps to lead to a final product having a higher concentration in TGF-beta (microfiltration, centrifugation, acidification, chromatography . . . ).

These additional purification steps allow the elimination of the insoluble whey proteins which are constituted predominantly by alpha-lactalbumin and immunoglobulins.

Preferred Embodiment for the Preparation of a Starting Solution Rich in Whey Proteins In an advantageous embodiment of the present invention, the starting solution rich in whey proteins is obtained by the following steps:
i) cross-flow microfiltration of skimmed milk on a membrane having a average pore size of 0.1 μm in an equipment that allows uniform transmembrane pressure, and microfiltrate recovery;
ii) concentration of the microfiltrate obtained in step i) with ultrafiltration with diafiltration with a membrane having a cut-off comprised between 5000 daltons and 20000 daltons, such as those frequently used by a man skilled in the art to prepare protein concentrates from whey; and
iii) recovery of the ultrafiltration retentate diafiltrated.

Optionally, it may be carried out a dilution of the proteins contained in the ultrafiltration retentate diafiltrated in order to obtain the starting whey protein solution, such as described in the present invention.

Preferentially, the cross-flow microfiltration is carried out with a Membralox type membrane (which is made of alumina alone or alumine-zircone mixture) 0.1 μm classic which requires the processing in a microfiltration equipment with co-current recirculation of the microfiltrate (hydraulic concept of the so-called uniform transmembrane pressure) or with a Membralox 0.1 μm membrane of reference GP such as the ones commercialized by the society EXEKIA.

The retentate obtained following the step i) of cross-flow microfiltration mainly contains milk caseins under a micellar form.

The microfiltrate obtained at the end of step i) essentially contains soluble milk proteins, lactose, non-protein nitrogen forms and soluble mineral salts.

The microfiltrate of step i) is submitted to an ultrafiltration step by diafiltration for concentration of the whey proteins. Preferentially, ultrafiltration is carried out with membranes with a cut-off comprised between 1 and 20 kD, more preferentially close to 5 kD.

Diafiltration is carried out preferentially with osmosis water, the diafiltration volume being comprised between 2 and 6 diavolumes, preferentially close to 4 diavolumes.

The ultrafiltrate contains soluble nitrogen from milk (non-protein nitrogen), lactose, and mineral salts.

For example, the ultrafiltration retentate obtained after step iii) contains approximately 200 g of total proteins per liter of retentate.

After the retentate recovery, proteins contained in the latter are diluted to obtain the starting whey protein solution. The dilution is preferentially carried out with osmosis water.

If necessary, the ultrafiltration retentate recovered in step iii) containing the proteins at a concentration of 200 g/l can be dried under a powder form before being used as a starting material in the method for obtaining a protein fraction highly enriched in TGF-beta according to the invention.

Protein Fraction Highly Enriched in TGF-Beta

Another object of this invention consists of a protein fraction highly enriched in TGF-beta characterized in that it comprises a concentration in TGF-beta 2 in activated form higher than 5 µg/g of total proteins.

Preferentially, the protein fraction highly enriched in TGF-beta above has a concentration in TGF-beta 2 comprised between 6 µg and 15 µg of TGF-beta 2 in activated form per gram of total proteins.

Preferentially, the fraction highly enriched in TGF-beta comprises a concentration in TGF-beta 2 in activated form comprised between 7 µg and 13 µg, advantageously between 8 µg and 12 µg and in the most preferred embodiment between 9 µg and 11 µg of TGF-beta 2 per gram of total proteins.

The concentration in TGF-beta 2 of the protein fraction enriched according to the invention can be easily determined by a man skilled in the art, for example by the use of an immunological test with specific antibodies of TGF-beta 2 like those commercialized by Société R & D SYSTEMS (Barton Lane, Oxon, OX14345, United Kingdom) under the brand of QUANTIKINE™.

The applicant showed that the whey proteins contained in the protein fraction highly enriched in TGF-beta are mainly constituted of alpha-lactalbumin and immunoglobulins.

Thus, the protein fraction highly enriched in TGF-beta according to the invention contains about 45 to 80 weight % of alpha-lactalbumine and between 10 and 25% of immunoglobulins, relatively to the total weight of the fraction.

Moreover, this protein fraction enriched in TGF-beta is almost generally free (less than 11%) of beta-lactoglobulin, a protein well-known for its allergenic properties.

This low concentration in beta-lactoglobulin in the protein fraction highly enriched in TGF-beta according to the invention allows its use for humans or animals.

Moreover, without wishing to be bound by any particular theory, the applicant believes that the high concentration in alpha-lactalbumin in the protein fraction highly enriched in TGF-beta according to the invention can significantly reinforce the therapeutic properties of TGF-beta.

Indeed the alpha-lactalbumin is rich in tryptophan since it contains four residues of this amino-acid per protein molecule. The alpha-lactalbumin is the milk protein with the highest content in this amino-acid. Tryptophan is a precursor of serotonin (5-hydroxytryptamine) and melatonin. Serotonin has sedative and anti-stress properties. Serotonin decreases the anxiety and helps to fall asleep. It is actually accepted that the stress plays a capital role in the development of psoriasis. Indeed patients suffering from psoriasis are submitted to a continuous stress. Combination of TGF-beta and alpha-lactalbumin makes particularly suited the protein fraction highly enriched in TGF-beta according to the invention for the development of drugs against psoriasis.

Moreover, the alpha-lactalbumin contains also a peptide starting from the amino acid in position 50 and ending at the amino acid in position 53, which has morphinomimetic properties. This opioid peptide derived from alpha-lactalbumin is called "alpha-lactorphin" (see Ciba H. and Yoshikawa M., Biological Functional Peptides from Food Proteins: New Opioides Peptides from Milk Proteins. Prot. Tail for Food and Med. Uses, Ed. M. Dekka, N.Y., 1986, pp 123-153).

Moreover, the alpha-lactalbumin has bactericidal properties. Its hydrolysis in the intestinal tract by trypsin and chymotrypsin induces the production of bactericidal peptides (see Pellegrini A. et al., Isolation and Identification of Fluid Bactericidal Domains in the Bovine Alpha-Lactalbumin Molecule, Biochim. Biophys. Acta, 1999, 1426: 439-448). Bactericidal properties of alpha-lactalbumin can be beneficial for patient with psoriasis. Indeed, pathogenic agents, such as Streptococcus and Staphylococcus, produce superantigens, which are bacterial toxins that cause activation and hyperproliferation of blood T-lymphocytes, that lead to a surge of activated T-lymphocytes at the skin level. From this surge results the activation and the proliferation of keratinocytes, which is the cell proliferation which forms the basis of psoriasis.

Without wishing to be bound by any particular theory, the applicant believes that the bactericidal activity of alpha-lactalbumin can be used to limitate the proliferation of keratinocytes that follows a bacterial infection, and then potentiate the effects of TGF-beta against psoriasis.

Moreover, the presence of alpha-lactalbumin, associated with TGF-beta, is likely to increase the stability of the TGF-beta in a protein fraction or in a composition according to the invention, and especially to protect the TGF-beta from diverse degradations by proteolytic enzymes, as for example when the fraction or the composition is administered to a patient.

Pharmaceutical Compositions According to the Invention

Another object of the invention consists of a pharmaceutical composition comprising a protein fraction highly enriched in TGF-beta, such as those described above, if necessary in combination with one or more physiolocally compatible excipients.

A pharmaceutical composition according to the invention is moreover characterized in that it contains a therapeutically efficient amount of TGF-beta.

According to another characteristic, a pharmaceutical composition according to the invention contains a therapeutically efficient amount of a combination between TGF-beta and alpha-lactalbumin.

If used for topical administration, a pharmaceutical composition according to the invention comprises preferentially between 1 nanogram and 1 mg of TGF-beta 2 per dose, more preferentially between 10 nanograms and 100 µg of TGF-beta 2 per dose, and in the most preferred embodiment between 50 nanograms and 20 µg of TGF-beta 2 per dose.

If used for systemic administration, the pharmaceutical composition according to the invention is adapted for daily administration between 1 nanogram and 500 µg of TGF-beta 2 per kg of the patient's weight, preferentially between 80 nanograms and 100 µg per kg of the patient's weight and in the most preferred embodiment between 1 µg and 20 µg per kg of the patient's weight.

The pharmaceutical composition according to the invention can be in the form of tablets, lozenges, hard gelatin capsules, powder bags, solutions for injectable preparation, lotions, pomades, dermatological creams, ointments, bandages, emulsions, intranasal or bronchial aerosols, implants, toothpastes or mouthwashes.

A pharmaceutical composition according to the invention can be applied by topical way. Such composition can also be administered locally or by a systemic route.

Particularly, a pharmaceutical composition such as defined above can be administered by oral, enteral, parenteral, intradermic, sub-cutaneous or intravenous route.

A pharmaceutical composition according to the invention comprises, in addition to a therapeutically efficient amount of TGF-beta 2 or to a combination of TGF-beta 2 and alpha-lactalbumin, also diluting agents, preservative agents, solubilization agents, emulsifier agents, adjuvants or physiologically compatible vehicles. Such compositions can be liquid or solid. They can be in the form of lyophilized formulations or dried powder formulations.

Such pharmaceutical compositions advantageously contain buffered diluants (e.g. tris-HCl, acetate, phosphate), additives such as albumin or gelatin in order to prevent adsorption onto surfaces, detergents (e.g. Tween 20™, Tween 80™, Pluronic S68™), biliary acid salts, solubilization agents (e.g. benzylic alcohol), charged agents or modifying compounds of tonicity (e.g. lactose, mannitol).

A pharmaceutical composition according to the invention can also be presented in formulations based on particles of polymeric compounds such as polylactic acid, polyglycolic acid, polyvinylpyrrolidone, or in the form of liposomes, microemulsions, micelles, or monolayer or multilayer vesicles.

Optionally, a pharmaceutical composition according to the invention can also comprise other constituents: additives such as antioxidants like ascorbic acid, polypeptides of low molecular weight (less than 10 amino-acids) such as polyarginines. It can also comprise amino acids such as glycine, glutamic acid, aspartic acid or arginine. It can also contain chelating agents such as EDTA. It can also comprise hydroxylated sugars such as mannitol or sorbitol.

For pharmaceutical compositions with controlled release or delayed release, fatty acids, waxes or oils are added. Pharmaceutical compositions in the form of particles whereas the protein fraction enriched in TGF-beta is covered by polymers such as poloxameres or poloxamines are equally part of the invention.

Compositions for topical formulations include gels, creams, solutions, emulsions, including carbohydrates polymers or biodegradable matrices of thereof. For the realization of the pharmaceutical composition according to the invention, the protein fraction highly enriched in TGF-beta can be encapsulated in wax, film or solid vehicle, comprising a chewing gum.

The pharmaceutical composition according to the invention can also be immobilized to impede its dilution by saliva, by agents such as methyl-propyl-cellulose.

The pharmaceutical composition according to the invention has several other clinical applications which some of them, but not limited to, are mentioned below.

TGF-beta has remarkable healing properties. A protein fraction highly enriched in TGF-beta according to the invention can advantageously be applied in the treatment of internal or external wounds, if necessary after surgery, or in the treatment of eschars or for the bones consolidation after a fracture.

The protein fraction according to the invention can also be applied in the treatment of osteoporosis because of the effects of TGF-beta on osteoclasts and osteoblasts, causing an induction of the cartilage and the bone formation.

Because of the inhibitory effect of TGF-beta on epithelial cell proliferation, a protein fraction highly enriched in TGF-beta according to the invention can advantageously be applied for the treatment of melanomas, myelomas or lymphomas.

The protein fraction of the invention can also advantageously be used in association with vitamin D3 and retinoids for treatment of some types of leukemia. It can advantageously be applied for battles against some cancer types, particularly breast cancers.

Moreover, the protein fraction highly enriched in TGF-beta according to the invention can also be used for the preparation of a drug intended for the prevention or treatment of some auto-immune diseases.

It can also advantageously be applied for the prevention or treatment of lupus erythemateous, which is a skin ailment characterized by the presence of red spots or plaques covered by scales, by hyperkeratosis, by an inflammatory process linked to infiltration and activation of T-lymphocytes in the dermis, and leading to the production of auto-antibodies. Lupus erythemateous is a prototype of autoimmune diseases. Administration of a pharmaceutical composition according to the invention to patients with lupus erythemateous, by oral route, is susceptible to significantly improve their general condition.

Advantageously, a protein fraction highly enriched in TGF-beta according to the invention can also be used for the preparation of a drug for prevention or treatment of psoriasis. Psoriasis is a dermatitis with chronic evolution characterized by hyperproliferation of keratinocytes associated with abnormalities in their maturation. Proliferation of psoriatic keratinocytes is revealed by an increase of mitosis number and a shortening of the cell cycle. Moreover, the psoriatic epidermis is the centre of an inflammatory infiltrator related to a surge of activated T-lymphocytes and pro-inflammatory cytokine liberation. Because of its cytostatic, anti-inflammatory and immunosuppressive properties, the protein fraction highly enriched in TGF-beta according to the invention, when administered by oral route, constitutes a basic treatment of psoriasis.

It can also constitute a treatment for other ailments such as rheumatoid arthritis, osteoarthritis, severe myasthenia, uveitis. It can be contemplated to use for organ transplants to avoid, or at least reduce, graft rejections.

A protein fraction highly enriched in TGF-beta according to the invention can also be used in the making of a drug intended for the prevention or treatment of Crohn disease. This disease is characterized by the inflammation of the gut, a deterioration of antigen regulation of the class II major histocompatibility complex (MHC). The gut inflammation is related to an increase of the class II MHC antigens in the gut epithelium. This inflammation is the result of an autoimmune reaction of the gut or of disturbances of the immune regulation.

Such pharmaceutical composition, when orally administered, constitutes a basic treatment against Crohn disease.

The invention has equally for object the use of a protein fraction highly enriched in TGF-beta such as described above for the manufacture of a drug for prevention or treatment of diseases such as lupus erythematosus, psoriasis, Crohn disease, rheumatoic arthritis, osteo arthritis, severe myasthenia or uveitis.

It is also related to the use of a protein fraction highly enriched in TGF-beta for the manufacture of a drug intended for prevention or treatment of graft reject.

The invention also concerns the use of a protein fraction highly enriched in TGF-beta according to the invention for the manufacture of a drug intended for enhancing wound healing.

It also relates to the use of a protein fraction highly enriched in TGF-beta for the manufacture of a drug intended for prevention or treatment of osteoporosis.

According to another aspect, the invention relates to the use of a protein fraction highly enriched in TGF-beta for the manufacture of an oncostatic drug.

Moreover, the invention is illustrated, without being limited to, by the following examples:

EXAMPLES

Example I

Preparation of a Solution Rich in Whey Proteins (WPI) as a Starting Product for the Process According to the Invention 10,000 Kg of skimmed milk with a content in dry matter of 92.9 g/Kg and a content in N×6.38 of 35.4 g/Kg were introduced, at 50° C., in a microfiltration equipment comprising a 4.6 m$^2$ and 0.1 µm Membralox® membrane (alumine-zircone) and functioning with co-current recirculation of the microfiltrate such as to obtain a uniform transmembrane pressure of 0.6 to 0.7 bars.

The scanning rate in the Retentate compartment was fixed at 7 m/s.

The microfiltrate extraction flux was fixed at 345 l/h. The retentate extraction flux was fixed at 172.5 l/h.

The 6670 l of microfiltrate obtained, with a content in dry matter of 57.8 g/Kg and a content in N×6.38 of 6.4 g/Kg, were cooled down at 10° C. and introduced in an ultrafiltration equipment comprising a 9.6 m$^2$ Koch® membrane, with a spiral conception, and having a cut-off of 5 Kd. The outlet pressure was fixed at 3.4 bars.

The extraction flux of the ultrafiltrate was fixed at 250 l/h, and that of the retentate at 12.5 l/h. The 334 l/h of retentate were continuously added to the 1336 l of osmosis water until elimination of this volume of water added in an ultrafiltrate form.

The final diafiltered retentate thus obtained had a protein content (N×6.38) of 101.0 g/Kg and a content in dry matter of 106.3 g/Kg. It was either used immediately for the preparation of the fraction enriched in TGF-beta or freezed at −30° C.

Example II

Preparation of a Fraction Highly Enriched in TGF-Beta Starting From a Solution Rich in Whey Proteins 200 Kg of the diafiltered retentate obtained according to Example I were diluted in 2000 l with osmosis water at a temperature of 20° C. in a tank equipped with a balde agitator.

After 10 minutes of stirring, 1800 ml of 6N HCl were progressively added until the lowering of the pH value from 7.25 to 4.6. Stirring was continued during 10-15 minutes. The solution was thermally treated at 63° C.-2 minutes and cooled down at 25° C. in an Actijoule® equipment by 1000 l aliquots. The 2000 l of the obtained suspension, heated at 35° C., were then microfiltered in continuous in an equipment with 4.6 m$^2$ STERILOX® membranes having a 1.4 µm average pore diameter with co-current recirculation of the microfiltrate in a manner to obtain a uniform transmembrane pressure between 0.4 and 0.8 bars in 4.5 hours.

The extraction flux of the microfiltrate was fixed at 400 l/h. No extraction of the retentate was performed.

When the retentate volume was close to the dead volume of the microfiltration equipment, 320 l of osmosis water were continuously added and extracted in a microfiltrate form.

The 53 Kg of diafiltered retentate obtained had a content in dry matter of 39.96 g/Kg and a protein content (N×6.38) of 39.14 g/Kg and a content in TGF-beta of 430.5 µg/Kg (thus 11 µg/g of proteins). They were freezed at −30° C. and lyophilized by aliquots of 10 Kg.

Example III

Quantitative and Qualitative Analysis of the Protein Fraction Highly Enriched in TGF-Beta According to the Invention 1 mg of the lyophilized powder obtained in the Example II was dissolved in 1 ml of milliQ water then diluted 5 times in buffer A. The analytical equipment used was a Waters 600 E HPLC chromatograph with a "source RPC 3 ml" column (Pharmacia®).

The two buffers used were:
Buffer A: Trifluoroacetic acid (TFA) 0.1%, and
Buffer B: TFA 0.09% in acetonitrile 90%.

50 µl of product were injected and the elution was carried out by a gradient of 30 to 100% of buffer B in 30 minutes with a flux of 2 ml/min (at room temperature). Detection was carried out at 214 nm. Treatment of chromatographic areas was carried out with a Nelson® software, which allowed the estimation of the content, when compared to the total proteins: 53% of alpha-lactalbumin, 0.03% of serum-albumin, 10.9% of beta-lactoglobulin and 18.3% of immunoglobulins.

The TGF-beta 2 content of the enriched fractions was determined by an immuno-assay method using specific monoclonal antibodies of TGF-beta 2 (Quantikine Kits commercialized by R & D Systems, Barton Lane, Oxon, 0X14 3Y5, U.K.).

We claim:

1. A protein fraction enriched in TGFβ2 in an activated form, said protein fraction comprising a) TGFβ2 in an activated form in a content higher than 5 micrograms per gram of total proteins of said protein fraction, b) whey proteins comprising α-lactalbumin being about 45-80% by weight of said protein fraction, and c) an immunoglobulin being about 10-25% by weight of said protein fraction, wherein said protein fraction is effective for treating psoriasis, wherein said protein fraction is obtained by the steps of: precipitating milk or whey by acid treatment at a pH ranging between 4 and 5.5, and at a temperature between 55° C. and 68° C. so as to obtain a precipitated suspension; and microfiltrating the precipitated suspension so as to obtain a microfiltration retentate containing the protein fraction enriched in TGFβ2 in an activated form.

2. A pharmaceutical composition comprising the protein fraction according to claim 1, in combination with one or several physiologically compatible excipients selected from the group consisting of diluting agents, preservative agents, solubilisation agents, emulsifier agents, adjuvants, and physiologically compatible vehicles.

3. The protein fraction of claim 1, wherein said TGFβ2 in an activated form is between 6 µg and 15 µg per gram of total proteins in said fraction.

4. The protein fraction of claim 1, wherein said TGFβ2 in an activated form is between 7 µg and 13 µg per gram of total proteins in said fraction.

5. The protein fraction of claim 1, wherein said TGFβ2 in an activated form is between 8 µg and 12 µg per gram of total proteins in said fraction.

6. The protein fraction of claim 1, wherein said TGFβ2 in an activated form is between 9 µg and 11 µg per gram of total proteins in said fraction.

7. The protein fraction of claim 1, wherein said protein fraction contains less than 11% by weight of β-lactoglobulin of total protein fraction.

* * * * *

UNITED STATES PATENT AND TRADEMARK OFFICE
CERTIFICATE OF CORRECTION

PATENT NO. : 8,937,043 B2  Page 1 of 1
APPLICATION NO. : 11/181139
DATED : January 20, 2015
INVENTOR(S) : Jean-Louis Maubois et al.

It is certified that error appears in the above-identified patent and that said Letters Patent is hereby corrected as shown below:

On the title page, (73) Assignee:, delete "Piere" and insert --Pierre--

Signed and Sealed this
Fifth Day of May, 2015

Michelle K. Lee
*Director of the United States Patent and Trademark Office*